United States Patent
Chien

(10) Patent No.: US 7,099,778 B2
(45) Date of Patent: Aug. 29, 2006

(54) METHOD FOR DETERMINING DIFFUSIVITY AND MOLECULAR WEIGHT IN A MICROFLUIDIC DEVICE

(75) Inventor: Ring-Ling Chien, San Jose, CA (US)

(73) Assignee: Caliper Life Sciences, Inc., Mountain View, CA (US)

( * ) Notice: Subject to any disclaimer, the term of this patent is extended or adjusted under 35 U.S.C. 154(b) by 235 days.

(21) Appl. No.: 10/747,066

(22) Filed: Dec. 30, 2003

(65) Prior Publication Data

US 2005/0148093 A1    Jul. 7, 2005

(51) Int. Cl.
*G01N 31/00*  (2006.01)
*G06F 19/00*  (2006.01)
*B01L 3/02*   (2006.01)
*B01L 11/00*  (2006.01)
*B32B 27/04*  (2006.01)

(52) U.S. Cl. ............ 702/23; 422/50; 422/58; 422/68.1; 422/81; 422/82.05; 422/100; 422/101; 422/102; 422/103; 422/104; 422/110; 436/43; 436/52; 436/63; 436/164; 436/172; 73/1.01; 73/1.02; 702/1; 702/19; 702/22; 702/27; 702/28; 702/29

(58) Field of Classification Search ............ 422/50, 422/58, 68.1, 81, 82.05, 100, 101, 102, 103, 422/104, 110; 436/43, 52, 63, 164, 172; 73/1.01, 1.02; 702/1, 19, 22, 23, 27, 28, 702/29

See application file for complete search history.

(56) References Cited

U.S. PATENT DOCUMENTS

| | | | |
|---|---|---|---|
| 6,171,865 B1 * | 1/2001 | Weigl et al. ............ | 436/52 |
| 6,454,945 B1 * | 9/2002 | Weigl et al. ............ | 210/634 |
| 6,541,213 B1 | 4/2003 | Weigl et al. | |
| 6,582,963 B1 | 6/2003 | Weigl et al. | |
| 6,613,580 B1 * | 9/2003 | Chow et al. ............ | 436/180 |
| 6,991,713 B1 * | 1/2006 | Adourian et al. ....... | 204/453 |

OTHER PUBLICATIONS

Kamholz, A., et al., "Quantitative Analysis of Molecular INteraction in a Microfluidic Channel: The T-Sensor," AnalChem, Dec. 1, 1999, pp. 5340-5347, vol. 71, No. 23.

Costin, et al., "Diffusion Coefficient Measurement in a Microfluidic Analyzer Using Dual-Beam Microscale-Refractive Index Gradient Detection—Application to on Chip Molecular Size Determination," Journal of Chromotagraphy A,, Sep. 27, 2003, pp. 77-91, vol. 1013, No. 1-2.

* cited by examiner

Primary Examiner—Jill Warden
Assistant Examiner—Brian Sines
(74) Attorney, Agent, or Firm—Donald R. McKenna; Ann C. Petersen

(57) ABSTRACT

The present invention is directed to a method for determining the molecular weight and diffusivity of a sample solute by providing a plus shaped microchannel network on a microfluidic chip, having at least four microchannels intersecting at a cross point; flowing a sample stream comprising a sample solute of unknown diffusivity and a blank stream from separate microchannels through the cross point and out to separate microchannels; creating a sample curve measuring the concentration of the sample solute that diffuses from the sample stream to the blank stream at the cross point while altering the flowrate of one of the blank stream or the sample stream; and determining a diffusion coefficient of the sample solute by extrapolating data from similar curves of at least two solutes having known molecular weights and/or diffusion coefficients created under similar conditions as those generated by the sample solute.

8 Claims, 5 Drawing Sheets

METHOD FOR DETERMINING DIFFUSIVITY AND MOLECULAR WEIGHT IN A MICROFLUIDIC DEVICE

FIELD OF THE INVENTION

This invention relates generally to a method for measuring diffusivity, i.e., diffusion coefficient, K, and molecular weight in microfluidic devices. The present invention can also be used to measure the extent of enzymatic, binding, hybridization, signaling or other reactions involving the separation of relatively small molecules from larger molecules, and/or for the separation of differently charged (and/or sized) species from one another.

BACKGROUND OF THE INVENTION

Recent efforts have been directed towards the development of microscale assay methods in which various chemical and biological processes may be examined in rapid succession and with small amounts of material. For example, microfluidic chips, which are chips of glass, silica or plastic contain a network of microscale channels through which fluids and chemicals are moved in order to perform the experiment. These chips use minute quantities of fluids or other materials, controllably flowed and/or directed, to generate highly reproducible and rapidly changeable microenvironments for control of chemical and biological reaction conditions, enzymatic processes, etc.

Microfluidic devices use a small volume of material. A plug of the material of interest, such as a molecule, compound, or biological compound or molecule such as a protein, analyte, or DNA molecule is introduced to a conduit and observed at least at some point along the channel. Several plugs of a variety of compounds are typically introduced into the same conduit separated by sufficient solvent or buffer material to distinguish the two plugs. However, as a plug of material moves along a conduit, a variety of forces causes the material of interest to disperse from a concentrated discrete plug into adjacent volumes of buffer or other solvent that separate the plug of material from adjacent sample plugs introduced into the conduit. Such forces include the laminar or parabolic velocity profile of a plug of material in a conduit and the molecular diffusivity of the particular material within a particular buffer or other solvent. Due to dispersion, a plug of material having a certain length and a certain concentration at the beginning of the conduit will have a longer length and be less concentrated at the end of the conduit.

One advantage of microfluidic devices is that a large variety of small plugs can be introduced and monitored within a conduit in rapid succession. The more plugs of material directed into a conduit at a time, the more tests can be run in a smaller amount of time. If the plugs of material are introduced too closely, however, dispersion may cause the solute in one sample plug to overlap the solute of a second adjacent sample plug by the time the plugs travel to the opposite end of the conduit. Thus, it is helpful to be able to adequately predict how the length of a plug will increase due to dispersion to maximize throughput, i.e., maximize the number of different samples plugs introduced to the conduit in a minimum amount of time, and minimize cross-contamination of adjacent sample plugs. U.S. Pat. No. 6,150,119, which is incorporated herein by reference in its entirety, provides further discussion of maximizing throughput.

Further, in very small microchannels, inertial effect, turbulence and other forces that typically affect streamlines in larger channels become negligible. Fluids flowing through a microchannel experience near laminar flow, or flow in distinct layers or streamlines. With laminar flow, streamlines do not intermix, other than by diffusion, across streamlines or between contacting streams. Thus, an accurate determination of molecular diffusivity for a particular sample is important for optimal development and use of microfluidic devices and techniques, particularly for predicting particle dispersion.

Taylor developed a method to measure molecular diffusion based on the mass flux in a capillary tube. See e.g., Taylor, Sir Geoffery, F. R. S. *Conditions of soluble matter in solvent flowing slowly through a tube*, Proc. Roy. Soc. (London) 219A:186–203 (1953) and Taylor, Sir Geoffrey, F. R. S., *Conditions under which dispersion of a solute in a stream of solvent can be used to measure molecular diffusion*, Proc. Roy. Soc. (London) A225: 473–477 (1954). In particular, he determined that the mass flux along the length of a capillary tube is a sum of convection forces and molecular diffusion. Aris developed a formula based on the work of Taylor for calculating the apparent diffusion coefficient, K. Aris, R., *On the dispersion of a solute in a fluid flowing through a tube*, Proc. Roy. Soc. (London) A235: 67–77 (1956). However, the Taylor-Aris formula was useful only for circular tubes and other shaped conduits with a known radius. However, it must be adapted for non-circular tubes, rectangular channels or other irregular shaped conduits, such as microfluidic channels. See Chatwin, P. C., et al., *The effect of aspect ratio on longitudinal diffusivity in rectangular channels*, Journal of Fluid Mechanics 120: 347–358 (1982). Because the Taylor-Aris dispersion formula requires complicated and rigorous viscosity calculations to determine the average velocity and requires making various assumptions in order to calculate the molecular diffusivity, the method is typically effective only for low velocity flow and small radial distances. Nonetheless, the method is still often used today for measuring molecular diffusivities.

Others have tried various other calculations based on the Taylor-Aris formulation. See e.g., Michael S. Bello, et al., *Use of Taylor-Aris Dispersion for Measurement of a Solute Diffusion Coefficient in Thin Capillaries*, Science 266:773–776 (1994). However, these methods still require extra steps to determine velocity.

Still others have determined molecular diffusivities by measuring a stream of solute in a single microchannel. See e.g., Andrew E. Kamholz, et al., *Optical Measurement of Transverse Molecular Diffusion in a Microchannel*, Biophys J 80(4):1967–1972 (April 2001). Further, U.S. Pat. Nos. 5,872,710 and 6,541,213, both to Weigl et al, and U.S. Pat. No. 5,932,100 to Yager et al., which are all incorporated herein by reference in their entirety, discuss how to manipulate diffusivities in a single microchannel to separate large and small particles, because larger particles diffuse more slowly than small particles. In general, these references teach having a sample solute stream and a blank stream, such as a stream of just a solvent or buffer, flow in distinct streamlines through a single microchannel. Smaller particles diffuse across streamlines creating a diffusion profile along the length of the channel. In order to measure the amount and rate of diffusion, small changes in concentrations must be measured in a single microchannel (generally in the middle of the channel) having a large background signal because the microchannel contains both diffused particles and undiffused particles. Further, these separation methods occur with both the blank stream and the sample stream having the same flowrate.

BRIEF SUMMARY OF THE INVENTION

The present invention is directed to a method for determining the molecular weight of particles in a sample stream by exploiting the differences in diffusivity for particles of different molecular weights. From the molecular weight, the diffusion coefficient, K, can be determined from a well-established correlation between molecular weight and the diffusion coefficient. In another method of the present invention, the diffusion coefficient may be directly determined based on similar diffusivity data measured from two or more samples of known diffusivity.

In particular, the present invention includes the steps of:

(a) providing an unknown sample solute stream;

(b) providing a blank stream; wherein at least one of the unknown sample solute stream and the blank stream comprises a detectable first indicator;

(c) allowing the unknown sample solute stream to contact the blank stream, such that a portion of the unknown sample solute in the unknown sample solute stream diffuses into the blank stream;

(d) creating a curve that represents concentration of the unknown sample solute that has diffused into the blank stream as a function of flowrate of at least one of the unknown sample solute stream and the blank stream; and (e) extrapolating diffusion coefficients of the unknown sample solute by comparing the curve to at least two curves created under similar conditions using solutes with known diffusion coefficients.

In another aspect of the present invention, a particular microfluidic chip is utilized having a plus-shaped microchannel network on a microfluidic chip, i.e., having at least four microchannels intersecting at a cross point. By flowing a sample stream comprising a sample solute having an unknown diffusivity from a first microchannel through the cross point into a second microchannel adjacent to the first microchannel and flowing a blank stream from a third microchannel through the cross point to a fourth microchannel adjacent to said third channel, the sample stream and the blank stream contact each other at the cross point but flow away from the cross point in different directions. Thus, any background fluorescence from the undiffused sample solute can be avoided.

In another aspect of the present invention, a sample solute can be run simultaneously with one, two or more solutes of a known molecular weight and/or having a known diffusion coefficient to account for variables in the geometries of different microfluidic chips.

Further features and advantages of the invention, as well as the structure and operation of various embodiments of the invention, are described in detail below with reference to the accompanying drawings. It is noted that the invention is not limited to the specific embodiments described herein. Such embodiments are presented herein for illustrative purposes only. Additional embodiments will be apparent to persons skilled in the relevant art(s) based on the teachings contained herein.

BRIEF DESCRIPTION OF THE FIGURES

The accompanying drawings, which are incorporated herein and form a part of the specification, illustrate the present invention and, together with the description, further serve to explain the principles of the invention and to enable a person skilled in the pertinent art to make and use the invention.

The present invention will be described with reference to the accompanying drawings. The drawing in which an element first appears is typically indicated by the leftmost digit(s) in the corresponding reference number.

DETAILED DESCRIPTION OF THE INVENTION

Figure 1:
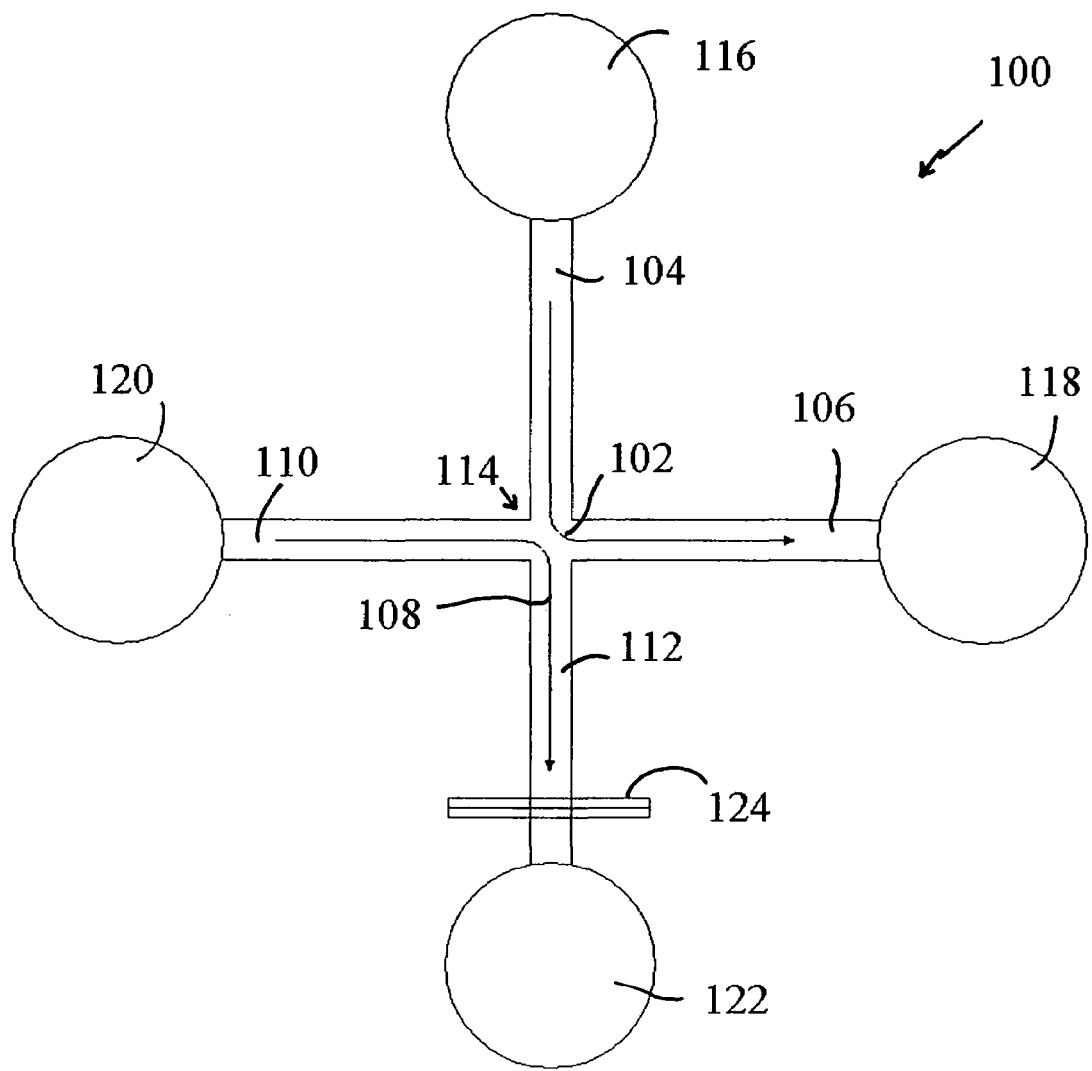
FIG. 1 is a schematic of a microchannel network formed on a microfluidic chip of the present invention.

Several methods for controlling the flow of materials on a microfluidic chip are well known in the art. For example, U.S. Patent Application Publication No. 2001/0052460, which is incorporated herein by reference in its entirety, discusses controlling and manipulating the flowrates of material through microchannels of a microfluidic network by applying, controlling and varying pressures at the different reservoirs located at the ends of the microchannels. Other methods of moving fluids through microchannels include acoustic streaming, i.e., using acoustic energy, and electrokinetics, i.e., utilizing the electrochemical forces of the sample molecules to move material in microchannels.

Thus, using one or more of these forces, it is possible to develop streamlines that are capable of making near 90-degree turns where microchannels come together or cross in a microfluidic network. For example, microfluidic network 100 shown in FIG. 1, has a generally plus (+) shape, wherein microchannels 104, 106, 110 and 112 meet at a cross point 114. A sample solute streamline 102 illustrates how a sample solute stream flows around a near 90 degree turn from a first microchannel 104 towards a second microchannel 106. Meanwhile, a blank streamline 108 illustrates how a blank stream flows around another near 90 degree turn from a third microchannel 110, which is opposite second microchannel 106, towards a fourth microchannel 112, which is opposite first microchannel 104.

At cross point 114, the solute stream and the blank stream come into contact with one another. Because streams in a microfluidic channel experience near laminar flow the streams do not cross, but solute from the sample solute stream diffuses into the blank stream at cross point 114 at a rate characteristic of the particular solute.

As discussed above, one way to control the direction and flowrate of the sample solute stream and the blank stream is to create a pressure differential between where the stream begins and where it ends. Thus, a greater pressure is applied to a solute introduction reservoir 116 located at an end of first microchannel 104 opposite from cross point 114 and a lower pressure is applied to a sample exit reservoir 118, located at an end of second microchannel 106 opposite from cross point 114. To equilibrate the pressure, sample solute molecules form a sample solute stream flowing from the sample introduction reservoir 116 towards the lower pressure at the sample exit reservoir 118. By adjusting the pressure differential between the sample introduction reservoir 116 and the sample exit reservoir 118, the sample solute stream will flow at a controlled flowrate.

Similarly, greater pressure can be applied to blank introduction reservoir 120, located at an end of third microchannel 110 opposite from cross point 114, and lower pressure can be applied to product exit reservoir 122, located at an end of fourth microchannel 112 opposite from cross point 114. Thus, the flowrate of the blank stream also is created and controlled by manipulating the pressure differential in the blank introduction reservoir 120 and product exit reservoir 122.

The amount of a solute that will diffuse from a sample solute stream to a blank stream depends on the amount of time that the two streams are in contact with one another. Thus, in the example shown in FIG. 1, if the flowrates of either the sample solute stream or the blank stream increase, less solute will diffuse into the blank stream because the stream will have a lower contact time at cross point 114. Similarly, if the flowrate of either stream decreases, a greater concentration of solute will diffuse into the blank stream from the sample solute stream, because the two streams will have a greater contact time at cross point 114.

In order to determine the amount of sample solute that has diffused from the sample solute stream to the blank stream of fourth microchannel 112, sample solute molecules must be identifiable by a detectable marker or labeling agent. Several indicators are suitable for the present invention, which may be suitable for a variety of solute molecules. Labeling agents may include fluorescent, phosphorescent, chemiluminescent, enzyme particles, and other labeling agents known in the art. Alternatively, as noted below, label-free methods can be used for detection, and/or the sample solute in the sample stream can be unlabeled while the blank stream includes a detectable label such as a labeled affinity molecule which has a specific affinity for the sample solute, as in the case of antibody-antigen binding reactions, ligand-receptor reactions, and enzyme-substrate reactions, whereby the complex of the affinity molecule and the sample solute in the blank stream is labeled.

Labeling agents may be small enough to provide label/solute particle complexes which are of similar size, or at least in the same order of magnitude, as the unlabeled solute particles so that diffusion coefficients of the labeled solute particles are roughly equivalent to diffusion coefficients of unlabeled solute particles. For example, a sample solute particle having a molecular weight of 10,000 might be labeled with a molecule having a molecular weight of about 100 to 1,000. The labeling particle should not be so large as to significantly change the diffusion properties of the binding particle/labeled solute complex. However, the present invention accounts for the fact that many solute particles may have an unknown molecular weight. In this case, any labeling particle will be sufficient so long as the molecular weight and diffusion coefficient of the labeling molecule are known.

The label may be soluble or insoluble in the fluid and may adhere to the solute particle by adsorption, absorption or chemical binding. For example, the labeling agent can be a conventional art-known dye, a metal particle, or any other detectable particle known to the art.

As discussed above, any detection means known to the art may be used for detecting the labeled molecule bound to the diffused solute in the blank stream, which will capture the particular type of label used. For example, in the case of fluorescent labels, suitable optical or electric detectors, such as spectrofluorometers, microplate readers, fluorescence microscopes, fluorescence polarization readers, photomultiplier tubes or photodiodes, fluorescence scanners, including microarray readers or flow cytometers may be used for detecting and measuring the intensity of the labels within a microchannel. Detection and analysis is done by any means known to the art, including both label and label-free detection techniques such as optical means, such as absorption spectroscopy, luminescence or fluorescence, by chemical indicators which change color or other properties when exposed to the sample solute, by immunological means, electrical means, e.g. electrodes inserted into the microfluidic chip, electrochemical means, radioactive means, thermal lens spectroscopy or virtually any microanalytical technique known to the art including magnetic resonance techniques, or other means known to the art to detect the presence of a sample solute such as an ion, molecule, polymer, virus, DNA sequence, antigen, microorganism or other factor. Preferably optical means are used, and antibodies, DNA sequences and the like are attached to optical markers.

Detection may also be accomplished by indirect detection via a detectable species in the blank stream such that the sample solute does not need to be labeled. For example, the blank stream could include a labeled affinity molecule which has a specific affinity for the sample solute of interest, such as an antigen which has a specific affinity for a sample antibody. The labeled affinity molecule in the blank stream may be any one which has a specific affinity for the solute in the sample, and for example may be selected from the group consisting of an antibody, an Fab or Fab' fragment of an antibody, an antibody variable region, a lectin, avidin, a receptor, an affinity peptide, an aptamer, and a DNA binding protein. The affinity molecule can have a specific affinity for ligands such as, e.g. virus particles, bacterial cells, proteins, peptides, carbohydrates, antigens, lipids, steroids, small chemicals, and so on, which, e.g., function as enzymes, antibodies, hormones, cytokines, structural components, signaling molecules, and ligands to a certain receptor, etc. and which are sometimes recognized as tumor markers, inflammation markers, and infectious disease markers. These include AFP, hCG, TSH, FSH, LH, interleukin, Fas ligand, CA19-9, CA125, PSA, HBsAg, anti-HIV antibody, T4, and/or like. Also they can include ligands conjugated to carrier proteins, ligands conjugated to nucleic acids, intracellular proteins, signaling molecules, and/or the like. The affinity molecule used in the invention includes, for example, those having a property capable of binding to the sample solute depending on a protein-protein interaction, a protein-chemical substance interaction, or a chemical substance-chemical substance interaction. Specifically, those binding based on an antigen-antibody interaction, a sugar chain-lectin interaction, an enzyme-inhibitor interaction, a protein-peptide chain interaction, a chromosome or nucleotide chain-nucleotide chain interaction, a nucleotide-ligand interaction or receptor-ligand interaction are included.

The blank stream could also include an intercalating dye where the sample solute of interest is DNA. Where the blank stream includes the detectable label, the detection means should include a measurement technique that is capable of measuring a detectable change in the signal emitted from the blank stream, such as fluorescence polarization detection which is a useful method of measuring binding among different molecules. The principles behind the use of fluorescent polarization are well known in the art and are set forth in more detail in commonly owned U.S. Pat. No. 6,287,774, the entire contents of which are incorporated by reference herein.

Returning to FIG. 1, a detector 124 is located along the fourth microchannel 112 and proximal to the product exit reservoir 122. Detector 124 produces a signal measuring the intensity of the indicator in the fourth microchannel 112. The detector's signal provides a quantitative measurement of the amount of sample solute molecules that have diffused into the blank stream.

The present invention provides a more accurate detection of the sample solute that diffused from the sample solute stream into the blank stream than prior methods because the blank stream flows into a separate microchannel directed in a direction away from the sample solute stream. Thus, any background fluorescence from the undiffused sample solute from the sample solute stream will not be picked up by the detector, which is focused only on the microchannel directing the flow of the blank stream containing the diffused solute molecules.

Using the apparatus and techniques discussed above, the method of the present invention involves quantitatively measuring the amount of a sample solute of an unknown molecular weight and/or diffusivity that has diffused from a sample solute stream into a blank stream while altering the flowrate in one of the streams. The molecular weight of an unknown sample solute can be extrapolated by comparing and curve fitting this quantitative measurement to similar quantitative measurements taken for other sample solutes having known molecular weights and/or diffusivities under the same conditions. This procedure will be discussed in further detail below with respect to specific examples.

EXAMPLE 1

Indicator Alone

Figure 2:
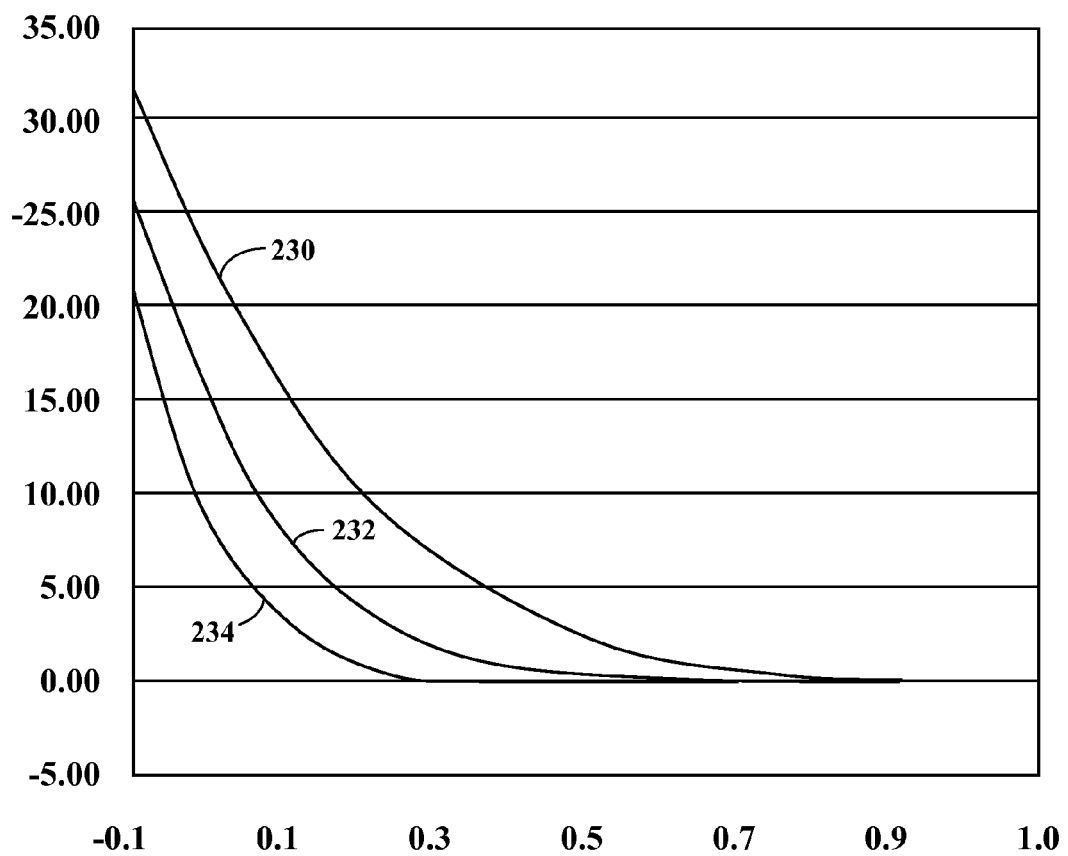
FIG. 2 graphically illustrates the diffusion of an indicator from a sample stream into a blank stream as a function of the flowrate of the blank stream, at three different flowrates of the sample stream.

A solution of fluorescein, a fluorescent molecule often used to bind to sample molecules, such as that commercially available from Molecular Probes, Inc., Eugene, Oreg., was introduced into a microchannel network 100, similar to that shown in FIG. 1, as the sample solute stream. The same solvent used for the fluorescein solution was used alone to create the blank stream. As the fluorescein sample stream contacted the blank stream, molecules of fluorescein diffused into the blank stream. A detector measured the intensity of the fluorescein that had diffused into the blank stream as the flowrate of the blank stream was changed by altering the pressure between the blank introduction reservoir 120 and the product exit reservoir 122, as discussed above with respect to FIG. 1. In the graph labeled FIG. 2, intensity measurements of fluorescein were plotted on the y-axis while a normalized change in pressure was plotted on the x-axis. As such, the graph of FIG. 2 illustrates the change in the concentration of diffused fluorescein as a function of the flowrate of the blank stream.

Curve 230 shows that as the pressure increased, and thus the flowrate of the blank stream increased, less of the fluorescein diffused into the blank stream. To form curve 230, the flowrate of the fluorescein stream was held constant at a first slow flowrate while only the flowrate of the blank stream was changed. Curve 232 also recorded the intensity of the fluorescein measured in the blank stream as the pressure, and thus the flowrate of the blank stream increased. In this case, however, the flowrate of the fluorescein stream was also increased to a second medium flowrate, faster than the first slow flowrate of curve 230. Similarly, curve 234 recorded the same data when the flowrate of the fluorescein stream was increased to a third fast flowrate. As you can see by the comparison between curves 230, 232 and 234, as the flowrates of both the blank streams and the fluorescein streams were increased, the contact time between the two streams at the cross point 114 was reduced, such that less fluorescein diffused into the blank stream.

Therefore, as an alternative, a similar curve may be generated that measures intensity of fluorescein in the blank stream as a function of the change in the flowrate of the fluorescein stream for three different controlled flowrates of the blank stream. Although the remaining examples use curves with axes similar to that of FIG. 2, either type of curve may be useful for the method of measuring the molecular weight and diffusivity of the present invention as would be apparent to one skilled in the art.

EXAMPLES 2 and 3

Known Molecular Weight Standards

Figure 3:
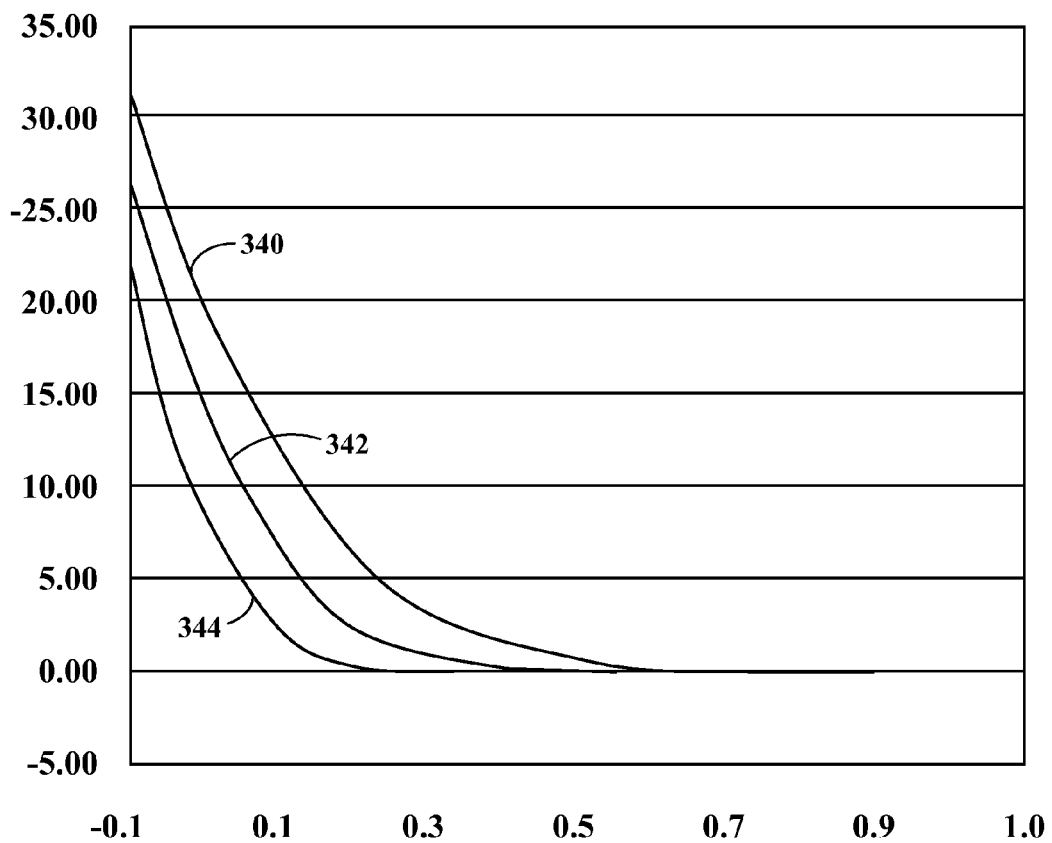
FIG. 3 graphically illustrates the diffusion of 3,000 kd molecules from a sample stream into a blank stream as a function of the flowrate of the blank stream, at three different flowrates of the sample stream.

Dextran conjugates, previously bound to fluorescein molecules, having known molecular weights of 3,000 kd and 40,000 kd are commercially available from Molecular Probes, Inc., Eugene, Oreg. (product numbers D-3305 and D1844). Solutions of the 3,000 kd and 40,000 kd dextran conjugates were introduced along with a blank stream into a microchannel network, such as that shown in FIG. 1, and intensity readings were taken as a function of the change in pressure applied to the blank stream, in the same manner as described above in Example 1 for the fluorescein stream. Intensity measurements of fluorescein are plotted against pressure data applied the blank stream and are shown in FIG. 3. Curves 340, 342 and 344 depict the amount of 3,000 kd dextran conjugates that diffused into a blank stream as a function of the change in flowrate of the blank stream. For curves 340, 342 and 344 the intensity measurements were taken with the 3,000 kd dextran conjugate stream flowing at the same first slow flowrate, second medium flowrate and third fast flowrate, respectively, as that for the fluorescein stream of Example 1.

Figure 4:
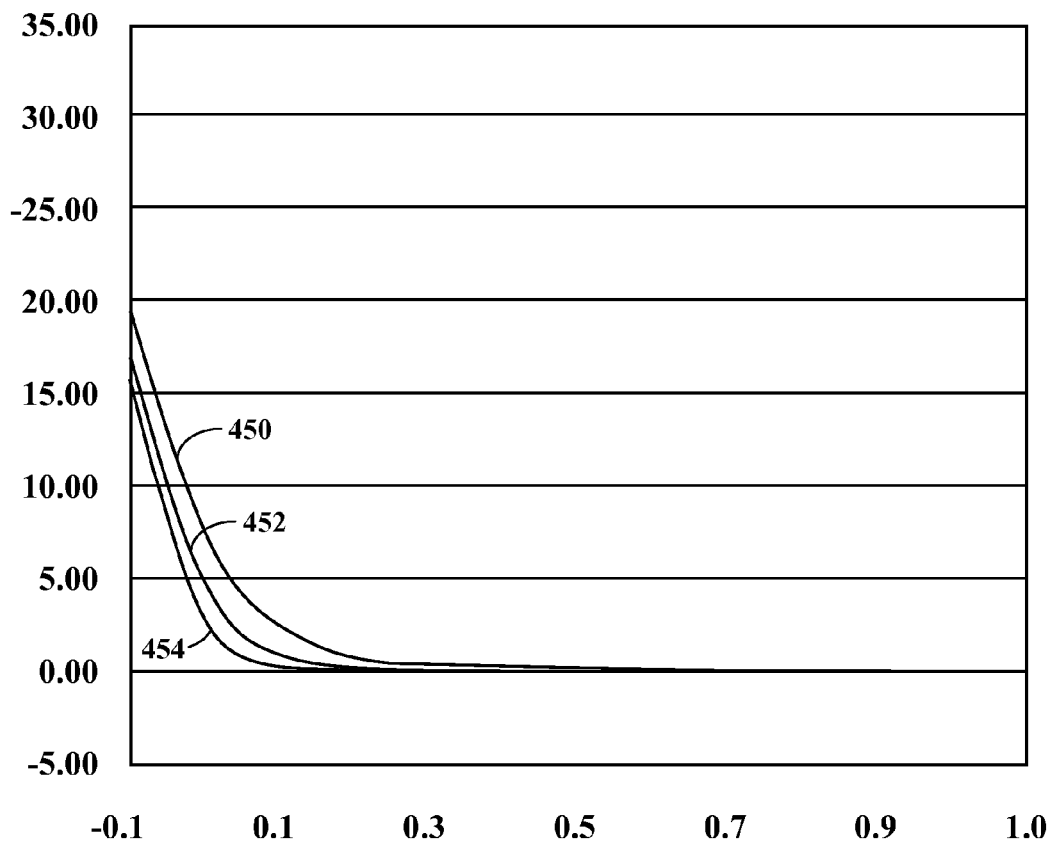
FIG. 4 graphically illustrates the diffusion of 40,000 kd molecules from a sample stream into a blank stream as a function of the flowrate of the blank stream, at three different flowrates of the sample stream.

Similarly, curves 450, 452 and 454 of FIG. 4 are measurements taken for a 40,000 kd dextran conjugate stream at the same first slow flowrate, second medium flowrate and third fast flowrate, respectively, as used in Example 1. As seen in FIGS. 3 and 4, varying the flowrates of the blank streams and the sample solute streams generate predictable results in the diffusivity behavior of solutes of different molecular weights.

Figure 5:
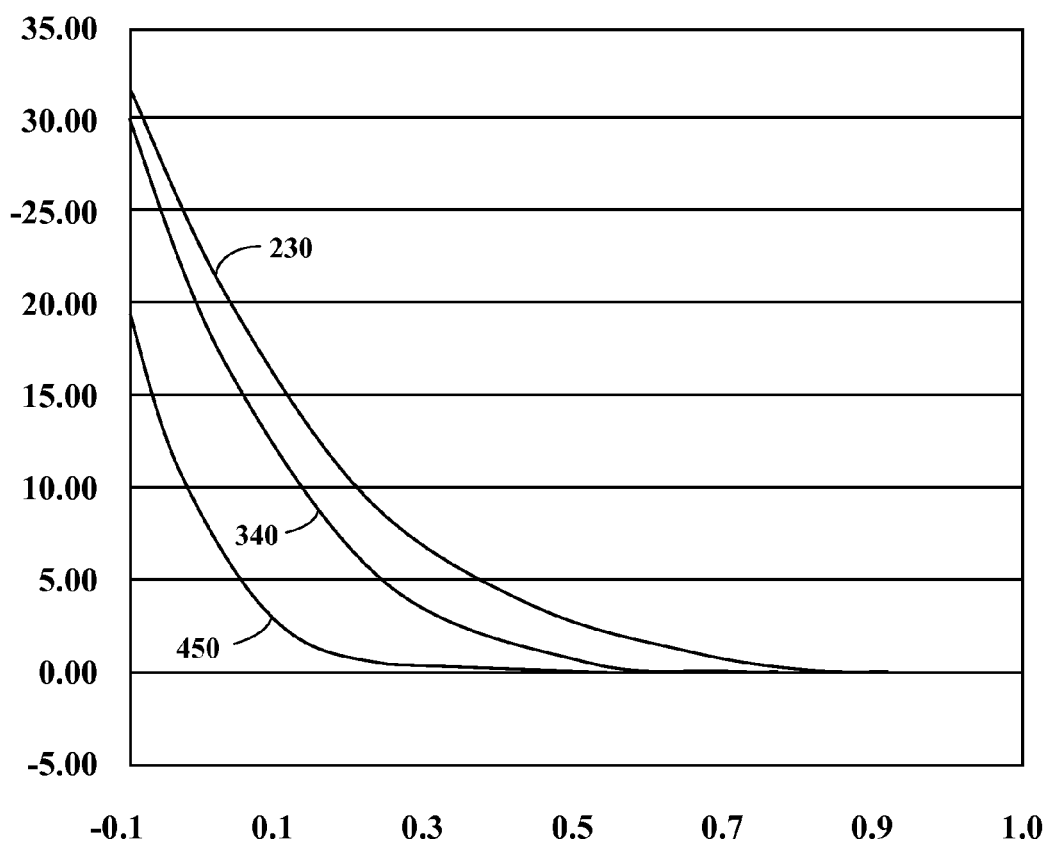
FIG. 5 graphically compares the diffusion of molecules of three different molecular weight molecules from three sample streams, respectively, into blank streams as a function of the flowrate of the blank streams.

FIG. 5 maps curve 230, the intensity measurement of the fluorescein stream, curve 340, the intensity measurement of the 3,000 kd dextran conjugate standard, and curve 450, the intensity measurement of the 40,000 kd conjugate standard, taken at the same constant first slow flowrate onto one graph. When comparing curves 230, 340 and 450, it is apparent that as the molecular weight increases, the diffusion of molecules between the sample stream and the blank stream decreases. FIG. 5 provides a molecular weight ladder to map changes in molecular weight. Other standards of known molecular weight and diffusivity are also available. Thus, repeating the experiments of Examples 1, 2 and 3, with various standards of known molecular weight creates additional data useful for determining the molecular weight of an unknown molecule.

By making the same intensity measurements for an unknown sample molecule under the same conditions as used in Example 1, molecular weight data can be interpreted from curve fitting and data analysis of the unknown sample curve with the curves for the standards of known molecular weight. For example, if a curve for an unknown sample was also plotted on FIG. 5, with the curve falling between curve 340 and 450, the molecular weight of the unknown sample may be interpreted to be between 3,000 kd and 40,000 kd. With curve fitting and data analysis, the molecular weight of the unknown sample may be extrapolated to find the molecular weight between 3,000 kd and 40,000 kd of the two known molecular weight standards. Once the molecular weight of the unknown sample is determined, the diffusivity, in particular, the diffusion coefficient, can be backed out using well known correlations between diffusion coefficients and molecular weight (for example, the Wilke-Chang Correlation). Alternatively, if diffusion coefficients are known for the standard samples, the diffusion coefficient for the unknown sample can be extrapolated from the curve fitting data directly because diffusivity is a direct function of molecular weight.

To remove variables, it is preferred that the same indicator, such as fluorescein, or another indicator with a molecular weight so close to fluorescein that the effect on diffusivity would be negligible, is bound to the unknown sample as is used for the standard samples. However, if this is not practical, data curves from sample streams of just the different indicators can be used to manipulate the data curves for the unknown and standard samples to account for molecular weight and diffusivity differences in the indicators. As an alternative, if the difference in molecular weight between the two indicators is known, the data can be manipulated using this information to take into account the use of different indicators.

Comparisons become easier if the same microfluidic chip, or chips with identical sizes and shapes of microchannels, is used to avoid variables in diffusivity caused by channels of different geometries. However, reusing the same chip takes time away from running multiple experiments concurrently and may not be desirable considering that many microfluidic chips are designed to be disposable rather than reusable. Thus, in an alternative method, the sample stream may comprise both molecules of an unknown molecular weight and molecules of a standard of known molecular weight such as those discussed above in Examples 2 and 3. In order to distinguish the diffused molecules of the standard from the unknown sample, the standard is bound to an indicator that is different and distinguishable from the indicator used for the unknown molecules. By simultaneously detecting both of the indicators, under the conditions discussed above in Example 1, the dependence of the response on the variation of chip and microchannel geometry is eliminated. The data recorded for the standard on this particular chip can be adjusted to match the data for the same standard in order to adjust the curves to compare to curves of solutes of known molecular weight. In an alternative method, two or more standards may be monitored simultaneously with the unknown sample so as to provide curve fitting data that is specific to each particular unknown sample run on a particular chip, thus information about the precise curve of the unknown can be extrapolated from the data for the two standards.

While the invention has been particularly shown and described with reference to preferred embodiments thereof, it will be understood by those skilled in the art that they have been presented by way of example only, and not limitation, and various changes in form and details can be made therein without departing from the spirit and scope of the invention. For example, changes in the plus (+) shaped design of the microfluidic chip may not alter the method used to determine molecular weight or diffusivity.

The microfluidic chip of the present invention may also be used, for example, to measure the extent of enzymatic, binding, signaling, hybridization or other reactions, e.g., receptor-ligand interactions, enzyme-substrate interactions, DNA hybridization reactions, and the like. For example, a binding reaction such as that between a protein and a fluorescently labeled ligand (or an antibody and a labeled antigen for immunoassays) could occur in first microchannel 104 (and/or reservoir 116 and/or off-chip), and then any unbound labeled ligand from the reaction could be separated from the bound protein-ligand complex by diffusion into blank stream 108 in FIG. 1. The amount of labeled ligand detected by detector 124 in fourth microchannel 112 could then be correlated to the extent of the binding between the protein and ligand. One or more test compounds could also be introduced into the microfluidic chip to determine the effect of the test compound(s) on the particular reaction of interest. For example, the device may be coupled to a sample introduction port, e.g., a pipettor, which serially introduces multiple samples or test compounds into the device for analysis. Examples of such sample introduction systems are described in e.g., U.S. Pat. No. 5,779,868 and published International Patent Application Nos. WO 98/00705, each of which is incorporated herein by reference in its entirety for all purposes.

The devices of the present invention are also useful for separating differently sized (and/or differently charged) molecules from one another by diffusion (as, described above), or can also be used to separate differently charged species from a sample mixture by controlling both the applied pressure as well as the electrical field in the channel network, as is described in co-pending U.S. patent application Ser. No. 10/386,900 entitled "Mixed Mode Microfluidic Systems," filed Mar. 4, 2003, the entire contents of which are incorporated by reference herein. As described therein, using a fluid control system with multiple pressure and voltage sources, the pressure and/or voltage in any given channel segment of the device can be controlled such that the hydrodynamic flow and electric field in any section of the microfluidic channel network can be set to desired values to extract and isolate components of interest.

For example, by applying a voltage gradient to electrodes placed in fluid contact with a fluid in reservoirs 116 and 122 of FIG. 1, an electric field can be established between reservoirs 116 and 122 such that selected species of a given electrophoretic mobility in the sample will be directed into fourth microchannel 112, while species having a lower electrophoretic mobility will follow the pressure flow path of sample solute stream 102 into second microchannel 106. Thus, mixtures of two or more sample species having different electrophoretic mobilities sent into channel cross point 114 can be separated substantially into separated components in separate channels of the intersection based on the different electrophoretic mobilities of the sample species. In such case, the reservoirs 116, 122 of the chip are adapted to be coupled to both a vacuum (or pressure) source and an electrode.

Examples of multi-port pressure control microfluidic devices and systems which include means for selectively and independently varying pressures and voltages within the reservoirs of the system can be found, for example, in co-pending U.S. patent application Ser. No. 09/792,435 entitled "Multi-Port Pressure Control Systems," filed Feb. 23, 2001, the entire contents of which are incorporated by reference herein. Where used, the electrodes, when placed in reservoirs 116 and 122, for example, may be formed on the substrate or formed independently, e.g., on an electrode plate for placement on the substrate for electrode contact with liquid in the associated reservoirs. Each electrode, in turn, is operatively coupled to a control unit or voltage controller (not shown) to control output voltage (or current) to the various electrodes.

The breadth and scope of the present invention should not be limited by any of the above-described exemplary embodiments, but should be defined only in accordance with the following claims and their equivalents. Additionally, all references cited herein, including issued U.S. patents, or any other references, are each entirely incorporated by reference herein, including all data, tables, figures, and text presented in the cited references.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and range of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

What is claimed is:

1. A method for determining the diffusivity of an unknown sample solute in a microchannel network, comprising the steps of:
    providing an unknown sample solute stream;
    providing a blank stream, wherein at least one of the unknown sample solute stream and the blank stream comprises a detectable first indicator;
    allowing said unknown sample solute stream to contact said blank stream, such that a portion of said unknown sample solute in said unknown sample solute stream diffuses into said blank stream;
    creating a curve that represents a concentration of said unknown sample solute that diffused into said blank stream as a function of flowrate of at least one of said unknown sample solute stream and said blank stream; and
    extrapolating diffusivity of said unknown sample solute by comparing said curve to at least two curves created under similar conditions using solutes of known diffusivity.

2. The method for determining the diffusivity of claim 1, wherein said first indicator is a fluorescent indicator.

3. The method for determining the diffusivity of claim 1, wherein said concentration of said unknown solute that has diffused into said blank stream is represented by a measurement of the intensity of said first indicator exhibited in said blank stream.

4. The method for determining the diffusivity of claim 1, wherein said flowrate of one of said blank stream and said unknown sample solute stream is represented by a normalized measurement of a pressure differential used to control the flowrate of said one of said blank stream and unknown sample solute stream.

5. The method for determining the diffusivity of claim 1, wherein said blank stream and said unknown sample solute stream contact each other at a cross point, where four microchannels intersect.

6. The method for determining the diffusivity of claim 5, further comprising:
    flowing said blank stream into which said unknown sample solute has diffused into a different microchannel than said sample solute stream.

7. The method for determining the diffusivity of claim 1, wherein said unknown sample solute stream includes a first standard solute of known diffusivity, said first standard sample solute is adhered to a second indicator, which is distinguishable from said first indicator.

8. The method for determining the diffusivity of claim 7, wherein said unknown sample solute stream includes a second standard solute of known diffusivity, said second standard solute is adhered to a third indicator, which is distinguishable from said first indicator and said second indicator.

* * * * *